United States Patent
Kuwabara et al.

(10) Patent No.: US 7,952,080 B2
(45) Date of Patent: May 31, 2011

(54) RADIATION DETECTING CASSETTE AND MEDICAL SYSTEM

(75) Inventors: Takeshi Kuwabara, Kanagawa (JP); Eiichi Kito, Kanagawa (JP); Tsuyoshi Tanabe, Kanagawa (JP); Takuya Yoshimi, Kanagawa (JP); Kazuharu Ueta, Tokyo (JP); Makoto Iriuchijima, Gunma (JP); Yasunori Ohta, Kanagawa (JP)

(73) Assignee: Fujifilm Corporation, Tokyo (JP)

( * ) Notice: Subject to any disclaimer, the term of this patent is extended or adjusted under 35 U.S.C. 154(b) by 0 days.

(21) Appl. No.: 12/801,749

(22) Filed: Jun. 23, 2010

(65) Prior Publication Data
US 2010/0259409 A1   Oct. 14, 2010

Related U.S. Application Data

(63) Continuation of application No. 12/219,908, filed on Jul. 30, 2008, now Pat. No. 7,767,981.

(30) Foreign Application Priority Data

Jul. 30, 2007 (JP) ................................. 2007-197220
Jun. 5, 2008 (JP) ................................. 2008-148031

(51) Int. Cl.
*H05B 33/00* (2006.01)
*H01L 25/00* (2006.01)
*G01N 23/04* (2006.01)

(52) U.S. Cl. .............. 250/484.4; 250/370.08; 250/580
(58) Field of Classification Search .............. 250/484.4, 250/580, 589, 591, 370.08, 370.09, 98.8, 250/162, 165, 205, 207
See application file for complete search history.

(56) References Cited

U.S. PATENT DOCUMENTS

| | | | |
|---|---|---|---|
| 5,572,566 | A | 11/1996 | Suzuki et al. |
| 5,877,501 | A | 3/1999 | Ivan et al. |
| 6,901,159 | B2 | 5/2005 | Baertsch et al. |
| 7,242,005 | B2 | 7/2007 | Funabashi |
| 2001/0055017 | A1 * | 12/2001 | Ording .......................... 345/440 |
| 2005/0108055 | A1 | 5/2005 | Ott et al. |
| 2006/0054829 | A1 | 3/2006 | Tsuchino et al. |
| 2006/0202127 | A1 | 9/2006 | Ozeki |
| 2007/0173108 | A1 | 7/2007 | Niwa |

FOREIGN PATENT DOCUMENTS

| | | |
|---|---|---|
| EP | 1 591 950 A1 | 11/2005 |
| JP | 07-140255 | 6/1995 |
| JP | 2000-105297 | 4/2000 |
| JP | 2003-172783 | 6/2003 |
| JP | 2004-141240 | 5/2004 |
| JP | 2005-006979 | 1/2005 |

* cited by examiner

*Primary Examiner* — David P Porta
*Assistant Examiner* — Faye Boosalis
(74) *Attorney, Agent, or Firm* — Jean C. Edwards, Esq.; Akerman Senterfitt LLP

(57) ABSTRACT

An image capturing system includes a cassette having a radiation detector, an image memory, and a cassette controller, an image capturing apparatus, a display device, and a host computer. The cassette controller comprises a capacity value transmitter for transmitting a capacity value of the radiation image information to the host computer before transmission process, and an image transmitter for transmitting the radiation image information. The host computer comprises an indicator controller for controlling the display device to display an indicator representing the capacity value received from the cassette as the upper limit, and a bar controller for controlling the display device to display a bar moving toward the indicator and having a length corresponding to the received capacity value of the radiation image information while the radiation image information is being received.

15 Claims, 17 Drawing Sheets

RADIATION DETECTING CASSETTE AND MEDICAL SYSTEM

The present application is a Continuation Application of U.S. patent application Ser. No. 12/219,908, filed on Jul. 30, 2008 now U.S. Pat. No. 7,767,981, which claims priority from Japanese Patent Application No. 2007-197220, filed on Jul. 30, 2007 and Japanese Patent Application No. 2008-148031, filed on Jun. 5, 2008, the contents of all of which are herein incorporated by reference in their entirety

BACKGROUND OF THE INVENTION

1. Field of the Invention

The present invention relates to a radiation detecting cassette housing therein a radiation conversion panel for detecting a radiation that has passed through a subject and converting the detected radiation into radiation image information, and a medical system incorporating such a radiation detecting cassette.

2. Description of the Related Art

In the medical field, there have widely been used radiation image capturing apparatus which apply a radiation to a subject and guide the radiation that has passed through the subject to a radiation conversion panel so as to capture a radiation image. Known forms of the radiation conversion panel include a conventional radiation film for recording a radiation image by way of exposure, and a stimulable phosphor panel for storing a radiation energy representing a radiation image in a phosphor and reproducing the radiation image as stimulated light by applying stimulating light to the phosphor.

The radiation film with the recorded radiation image is supplied to a developing device to develop the radiation image, or the stimulable phosphor panel is supplied to a reading device to read the radiation image as a visible image.

In the operating room or the like, it is necessary to read out a recorded radiation image immediately from a radiation conversion panel after the radiation image is captured for the purpose of quickly and appropriately treating the patient. As a radiation conversion panel which meets such a requirement, there has been developed a radiation detector having solid-state detectors for converting a radiation directly into an electric signal or converting a radiation into visible light with a scintillator and then converting the visible light into an electric signal to read out a detected radiation image.

In a radiation image capturing system which incorporates a radiation conversion panel, the radiation image information detected by the radiation conversion panel is transmitted to a host computer. Technologies concerning such a radiation image capturing system are disclosed in Japanese Laid-Open Patent Publication No. 2003-172783, Japanese Laid-Open Patent Publication No. 2004-141240, and Japanese Laid-Open Patent Publication No. 2005-006979, for example.

According to the technology disclosed in Japanese Laid-Open Patent Publication No. 2003-172783, image data detected by a radiation detecting cassette which houses a radiation detector therein are converted into a wireless signal and transferred to an external signal receiver by an image data transfer means. Therefore, the radiation detecting cassette requires no wiring, is independent of a controller, is capable of capturing images at a position remote from the controller, and can be used conveniently. The image data can also be transferred by a cable which can be used to supply electric power as well.

According to the technology disclosed in Japanese Laid-Open Patent Publication No. 2004-141240, a radiation detecting cassette receives ordering information which instructs capturing of a radiation image from an external device, stores the received ordering information, and transmits an image signal output from a solid-state radiation detector in association with the stored ordering information to the external device. The disclosed radiation detecting cassette can greatly reduce the burden imposed on the radiological technician who captures the radiation image using the radiation detecting cassette.

According to the technology disclosed in Japanese Laid-Open Patent Publication No. 2005-006969, a radiation image capturing apparatus includes a wired communication unit for transmitting and receiving digital image data and image capturing control signals with an external circuit through a cable, and a wireless communication unit for transmitting and receiving digital image data and image capturing control signals with the external circuit by wireless. Simply by attaching or detaching the cable, different data communication systems and power supply methods can selectively be used to put more emphasis on either a higher data transmission rate or an easier handing of the radiation image capturing apparatus.

Conventional medical systems incorporating a radiation detecting cassette which houses a radiation detector therein do not have any means for displaying or maintaining the status of the transmission of image data. Since the conventional medical systems give the user no indication as to whether the transmission of image data from the radiation detector to the host computer is in progress or has been completed, the user may accidentally remove the battery from the radiation detecting cassette or the operator of the host computer may initiate a next process while the image data are being transmitted. Accordingly, the storage of the image data into the host computer may be interrupted or otherwise unreliable.

SUMMARY OF THE INVENTION

It is an object of the present invention to provide a radiation detecting cassette and a medical system which include a means for displaying or maintaining the status of the transmission of image data to transmit the image data reliably to a host computer, thereby to make the radiation detecting cassette more reliable in terms of communications and also to make the medical system more reliable in operation.

According to a first aspect of the present invention, there is provided a radiation detecting cassette comprising a casing, a radiation conversion panel housed in the casing for detecting a radiation that has passed through a subject and converting the detected radiation into radiation image information, a memory housed in the casing for storing the radiation image information converted by the radiation conversion panel, a communication unit housed in the casing for transmitting at least the radiation image information to an external device, a controller housed in the casing, and a communication sustaining unit housed in the casing, for keeping the radiation image information transmitted at least during a period of time in which the communication unit is transmitting the radiation image information.

According to a second aspect of the present invention, there is provided a medical system comprising a radiation detecting cassette comprising a casing, a radiation conversion panel housed in the casing for detecting a radiation that has passed through a subject and converting the detected radiation into radiation image information, a memory housed in the casing for storing the radiation image information converted by the radiation conversion panel, a communication unit housed in the casing for transmitting at least the radiation image information to an external device, and a cassette housed in the casing, an image capturing apparatus for radiating the radiation to the subject, a host computer for exchanging information with the radiation detecting cassette and controlling the image capturing apparatus, and a display device for displaying information from the host computer, wherein the cassette controller comprises a capacity value transmitter for transmitting a capacity value of the radiation image information to the host computer before the radiation image information is transmitted, and an image information transmitter for transmitting the radiation image information, and the host computer comprises an indicator controller for controlling the display device to display an indicator, which represents the capacity value received from the radiation detecting cassette as an upper limit, and a bar image controller for controlling the display device to display a bar image, which moves toward the indicator so as to have a length corresponding to the received capacity value of the radiation image information during a period of time in which the radiation image information is received.

The radiation detecting cassette and the medical system according to the present invention allow image data to be transmitted reliably to the host computer to increase the reliability of communications with the radiation detecting cassette and the reliability of the medical system.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

A radiation detecting cassette and a medical system according to the present invention as applied to a radiation image capturing system will be described below with reference to FIGS. 1 through 17.

Figure 1:
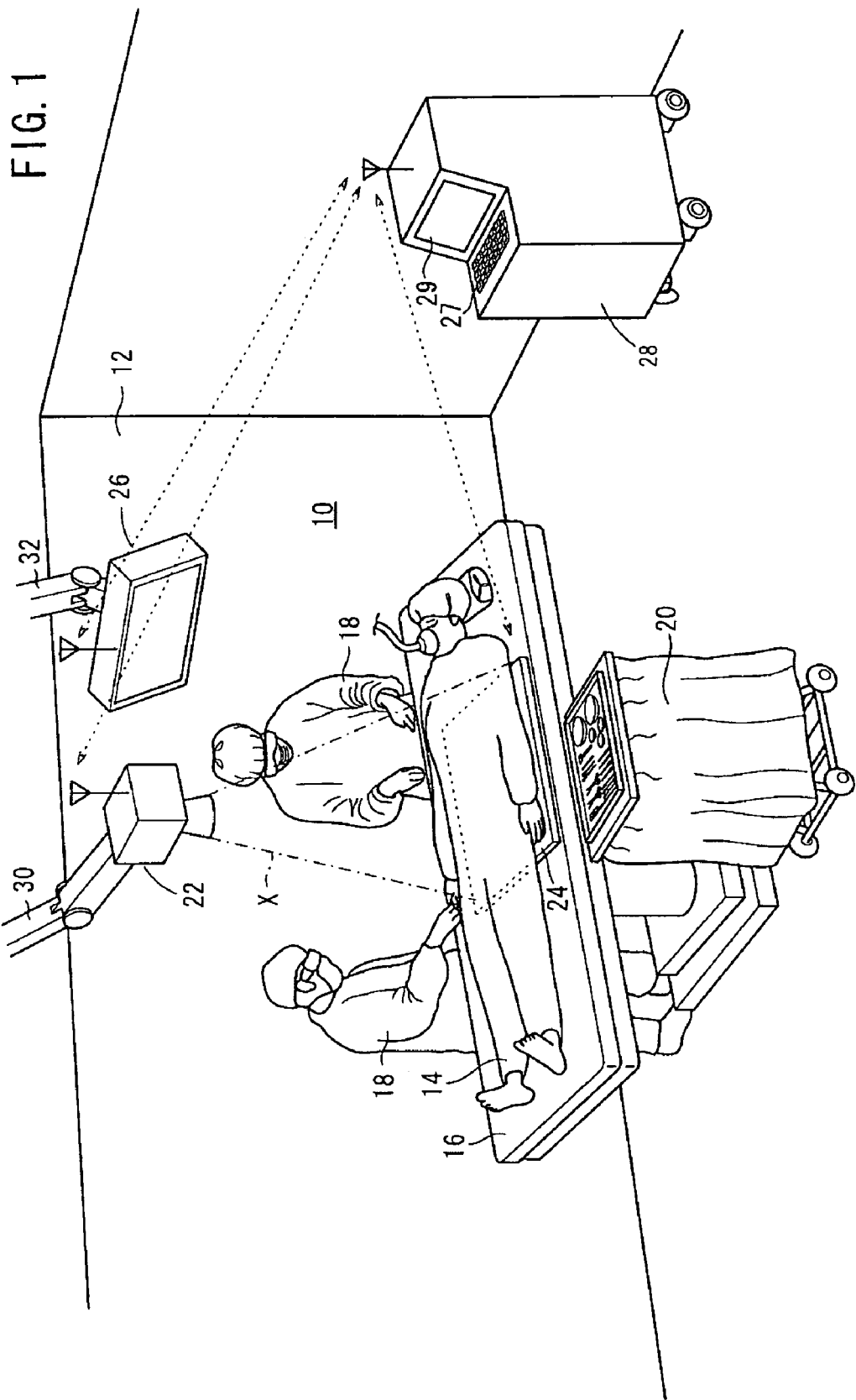
FIG. 1 is a perspective view inside an operating room incorporating a radiation image capturing system (image capturing system) according to an embodiment of the present invention.

FIG. 1 shows in perspective an operating room 12 incorporating a radiation image capturing system 10 (hereinafter also referred to as "image capturing system 10").

As shown in FIG. 1, the operating room 12 has, in addition to the image capturing system 10, a surgical table 16 for a patient (subject) 14 to lie thereon, and an instrument table 20 disposed to one side of the surgical table 16 for placing thereon various tools and instruments to be used by surgeons 18 operating on the patient 14. The surgical table 16 is surrounded by various apparatus required for surgical operations, including an anesthesia apparatus, an aspirator, an electrocardiograph, a blood pressure monitor, etc.

The image capturing system 10 includes an image capturing apparatus 22 for irradiating the patient 14 with a radiation X at a dosage according to image capturing conditions, a radiation detecting cassette 24 (hereinafter referred to as "cassette 24") housing therein a radiation detector, to be described later, for detecting the radiation X that has passed through the patient 14, a display device 26 for displaying a radiation image based on the radiation X that is detected by the radiation detector, and a host computer 28 for controlling the image capturing apparatus 22, the cassette 24, and the display device 26. The image capturing apparatus 22, the cassette 24, the display device 26, and the host computer 28 send and receive signals by way of wireless communications to and from each other. The host computer 28 includes a console 27 and a display 29.

The image capturing apparatus 22 is coupled to a first universal arm 30 so as to be movable to a desired position for capturing an image at a desired area of the patient 14, and also to be retractable to an out of the way position while the surgeons 18 are performing a surgical operation on the patient 14. Similarly, the display device 26 is coupled to a second universal arm 32 so as to be movable to a position where the surgeons 18 can easily confirm a captured radiation image displayed on the display device 26.

Figure 2:
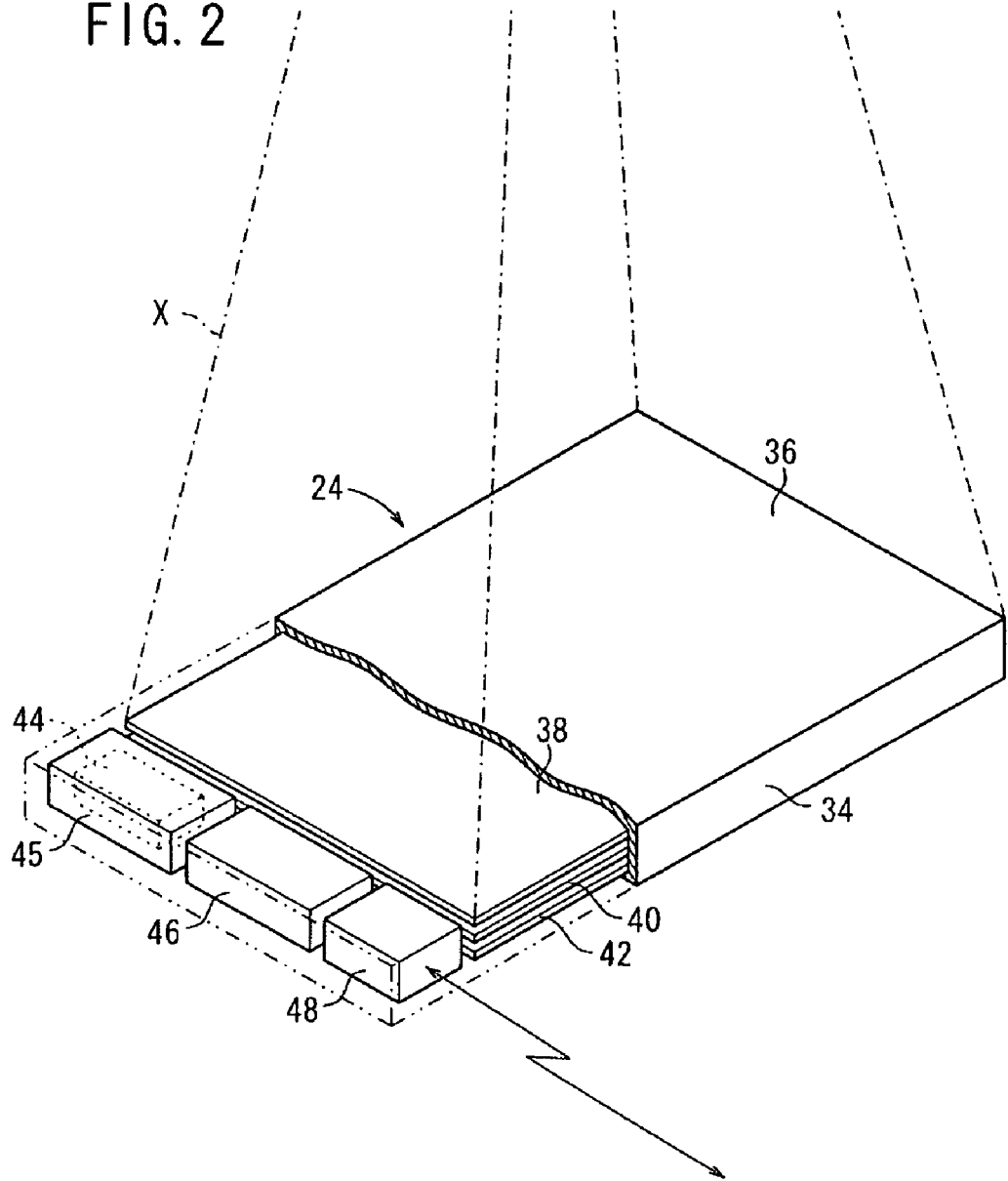
FIG. 2 is a perspective view, partly cut away, showing internal structural details of a radiation detecting cassette used in the radiation image capturing system.

FIG. 2 shows internal structural details of the radiation detecting cassette 24. As shown in FIG. 2, the radiation detecting cassette 24 has a casing 34 made of a material permeable to the radiation X. The casing 34 houses therein a grid 38 for removing scattered rays of the radiation X from the patient 14, a radiation detector (radiation conversion panel) 40 for detecting the radiation X that has passed through the patient 14, and a lead plate 42 for absorbing back scattered rays from the radiation X. The grid 38, the radiation detector 40 and the lead plate 42 are successively arranged in that order from an irradiated surface 36 of the casing 34 which is irradiated with the radiation X. The irradiated surface 36 of the casing 34 may be constructed as the grid 38.

The casing 34 also accommodates therein a battery pack 45 housing therein a battery 44 as a power supply of the cassette 24, a cassette controller 46 for energizing the radiation detector 40 with electric power supplied from the battery 44, and a communication unit 48 for sending and receiving signals including the information of the radiation X detected by the radiation detector 40, to and from the host computer 28. Under the irradiated surface 36 of the casing 34, a shield plate of lead or the like should preferably be placed over the side surfaces of the cassette controller 46 and the communication unit 48 to protect the cassette controller 46 and the communication unit 48 against damage which would otherwise be caused if those were irradiated with the radiation X.

Figure 3:
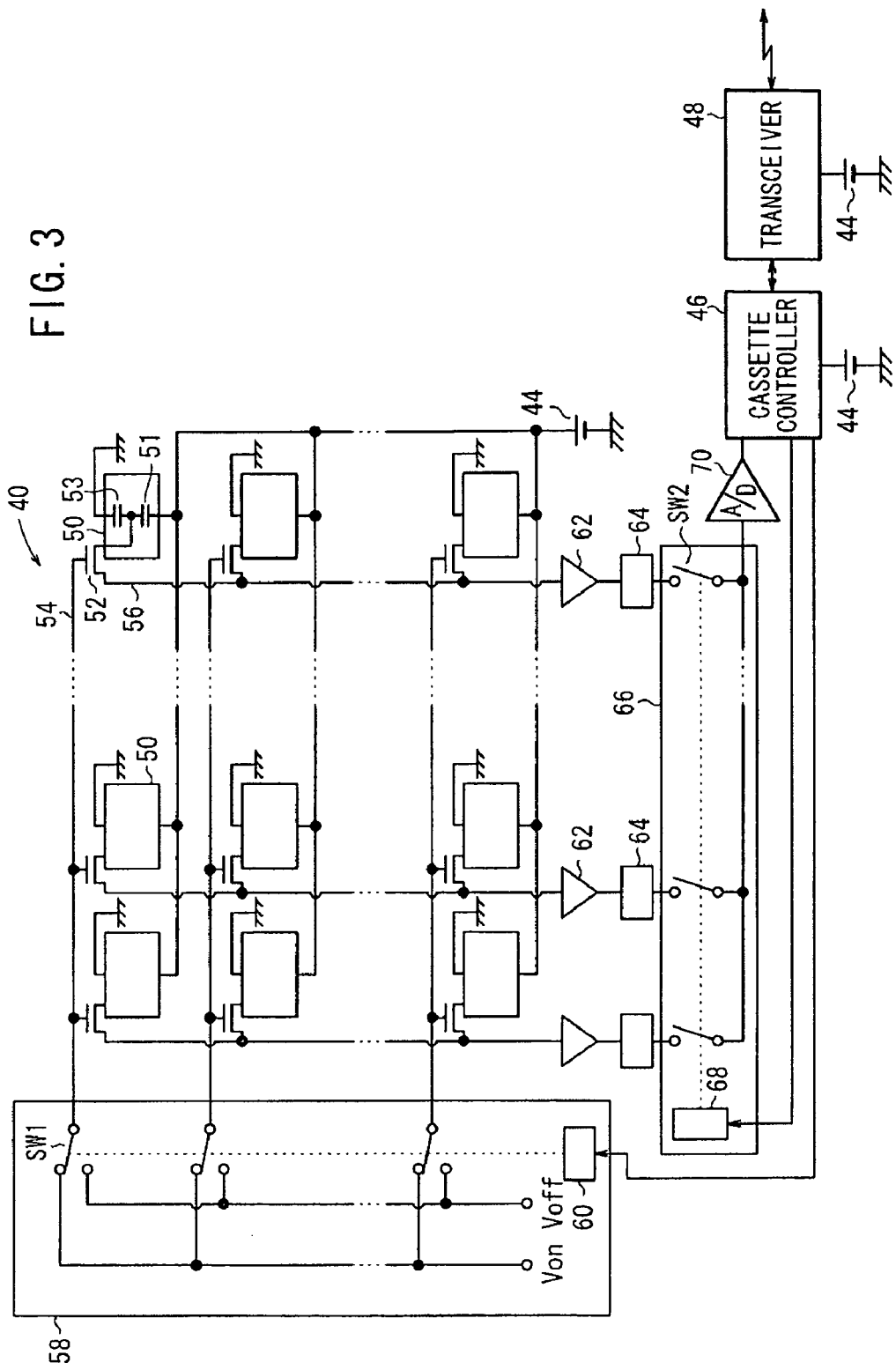
FIG. 3 is a block diagram of a circuit arrangement of a radiation detector of the radiation detecting cassette.

FIG. 3 shows in block form a circuit arrangement of the radiation detector 40. As shown in FIG. 3, the radiation detector 40 comprises an array of thin-film transistors (TFTs) 52 arranged in rows and columns, a photoelectric conversion layer 51 made of a material such as amorphous selenium (a-Se) for generating electric charges upon detection of the radiation X, the photoelectric conversion layer 51 being disposed over the array of TFTs 52, and an array of storage capacitors 53 connected to the photoelectric conversion layer 51. When the radiation X is applied to the radiation detector 40, the photoelectric conversion layer 51 generates electric charges, and the storage capacitors 53 store the generated electric charges. Then, the TFTs 52 are turned on along each row at a time to read out the electric charges from the storage capacitors 53 as an image signal. In FIG. 3, the photoelectric conversion layer 51 and one of the storage capacitors 53 are shown as a pixel 50, and the pixel 50 is connected to one of the TFTs 52. Details of the other pixels 50 are omitted from illustration. Since amorphous selenium tends to change its structure and lose its functionality at high temperatures, amorphous selenium needs to be used within a certain temperature range. Therefore, some means for cooling the radiation detector 40 should preferably be provided in the radiation detecting cassette 24.

The TFTs 52 connected to the respective pixels 50 are connected to respective gate lines 54 extending parallel to the rows and respective signal lines 56 extending parallel to the columns. The gate lines 54 are connected to a line scanning driver 58, and the signal lines 56 are connected to a multiplexer 66 serving as a reading circuit.

The gate lines 54 are supplied with control signals Von, Voff from the line scanning driver 58 for turning on and off the TFTs 52 along the rows. The line scanning driver 58 comprises a plurality of first switches SW1 for switching between the gate lines 54 and a row address decoder 60 for outputting a selection signal for selecting one of the first switches SW1 at a time. The row address decoder 60 is supplied with an address signal from the cassette controller 46.

The signal lines 56 are supplied with electric charges stored in the storage capacitors 53 of the pixels 50 through the TFTs 52 arranged in the columns. The electric charges supplied to the signal lines 56 are amplified by amplifiers 62 connected respectively to the signal lines 56. The amplifiers 62 are connected through respective sample and hold circuits 64 to the multiplexer 66. The multiplexer 66 comprises a plurality of second switches SW2 for switching between the signal lines 56 and a column address decoder 68 for outputting a selection signal for selecting one of the second switches SW2 at a time. The column address decoder 68 is supplied with an address signal from the cassette controller 46. The multiplexer 66 has an output terminal connected to an A/D converter 70. A radiation image signal generated by the multiplexer 66 based on the electric charges from the sample and hold circuits 64 is converted by the A/D converter 70 into a digital image signal representing radiation image information, which is supplied to the cassette controller 46.

Figure 4:
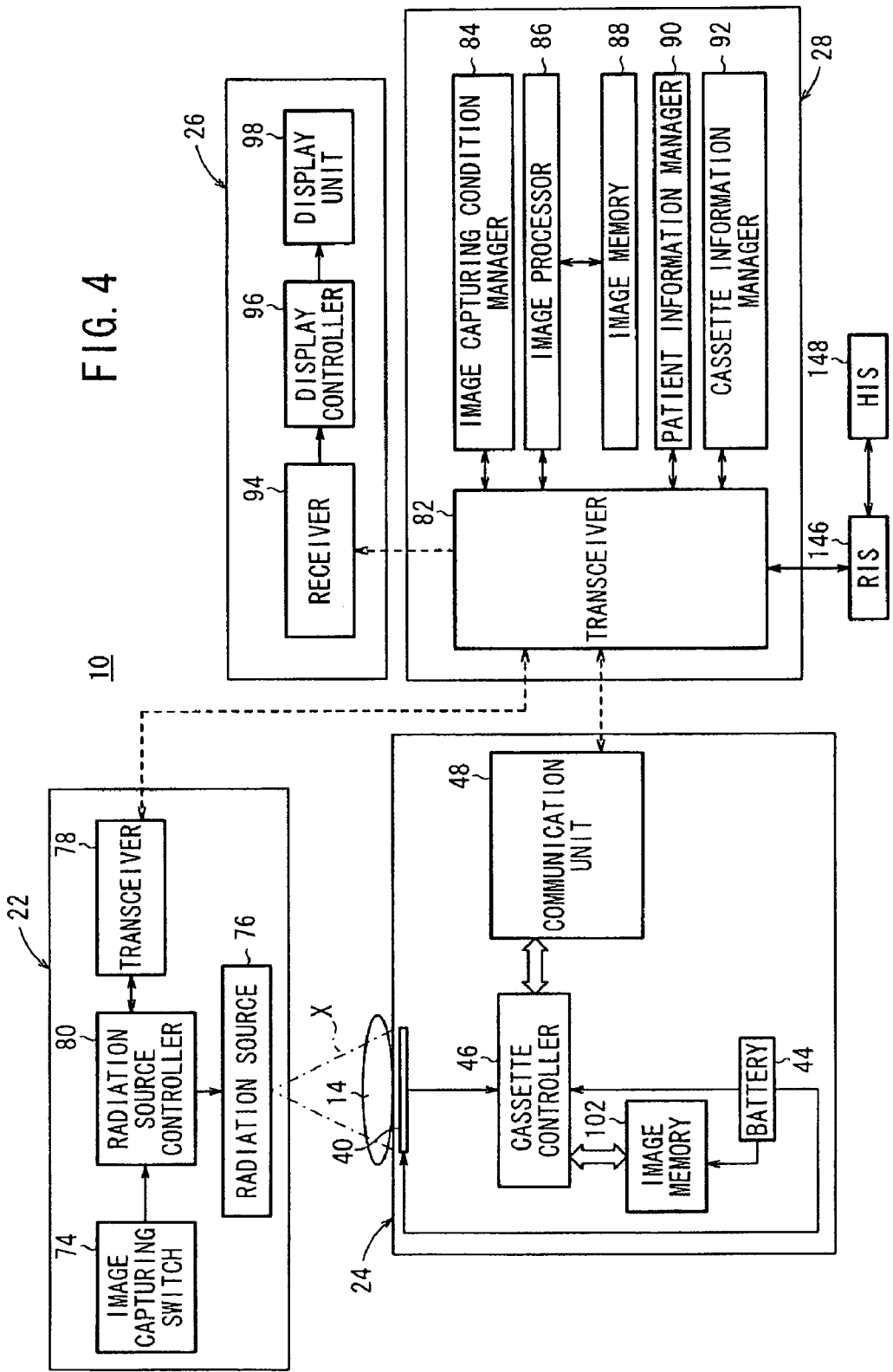
FIG. 4 is a block diagram of the radiation image capturing system according to the embodiment.

FIG. 4 shows in block form the image capturing system 10 which comprises the image capturing apparatus 22, the cassette 24, the display device 26, and the host computer 28. The host computer 28 is connected to a radiology information system (RIS) 146 which generally manages radiation image information handled by the radiological department of the hospital and other information. The RIS 146 is connected to a hospital information system (HIS) 148 which generally manages medical information in the hospital.

The image capturing apparatus 22 comprises an image capturing switch 74, a radiation source 76 for outputting the radiation X, a first transceiver 78 for receiving image capturing conditions from the host computer 28 by way of wireless communications and transmitting an image capturing completion signal, etc. to the host computer 28 by way of wireless communications, and a radiation source controller 80 for controlling the radiation source 76 based on an image capturing start signal supplied from the image capturing switch 74 and image capturing conditions supplied from the first transceiver 78.

The host computer 28 comprises a second transceiver 82 for transmitting and receiving necessary information including radiation image information to and from the image capturing apparatus 22, the cassette 24, and the display device 26 by way of wireless communications, an image capturing condition manager 84 for managing image capturing conditions required for the image capturing apparatus 22 to capture radiation images, a first image processor 86 for processing radiation image information transmitted from the cassette 24, an image memory 88 for storing the radiation image information processed by the first image processor 86, a patient information manager 90 for managing patient information of the patient 14 whose images are to be captured, and a cassette information manager 92 for managing cassette information transmitted from the cassette 24. The host computer 28 may be located outside of the operating room 12 insofar as it can transmit and receive signals to and from the image capturing apparatus 22, the cassette 24, and the display device 26 by way of wireless communications.

The image capturing conditions refer to conditions required for determining a tube voltage, a tube current, an irradiation time, etc. required to apply a radiation X at an appropriate dosage to an area to be imaged of the patient 14, and may be an area to be imaged, an image capturing method, etc., for example. The patient information refers to information about the patient 14 required to identify the patient 14, such as name, gender, age, patient ID number, etc. of the patient 14. Ordering information for instructing the capture of an image, including the image capturing conditions and the patient information can be set directly on the host computer 28 using the console 27 or can be supplied from an external source to the host computer 28 via the RIS 146.

The cassette information may include cassette ID information and information about the present status of the cassette 24 such as a remaining battery power level. If the cassette information is transmitted, together with the radiation image information, from the cassette 24, then the cassette information includes, in addition to the cassette ID information and the present status information, information about the radiation image information, e.g., an image number, an identification number of image capturing conditions, etc.

The display device 26 comprises a receiver 94 for receiving radiation image information from the host computer 28, a display controller 96 for controlling the display of the received radiation image information, and a display unit 98 for displaying the radiation image information processed by the display controller 96.

Figure 5:
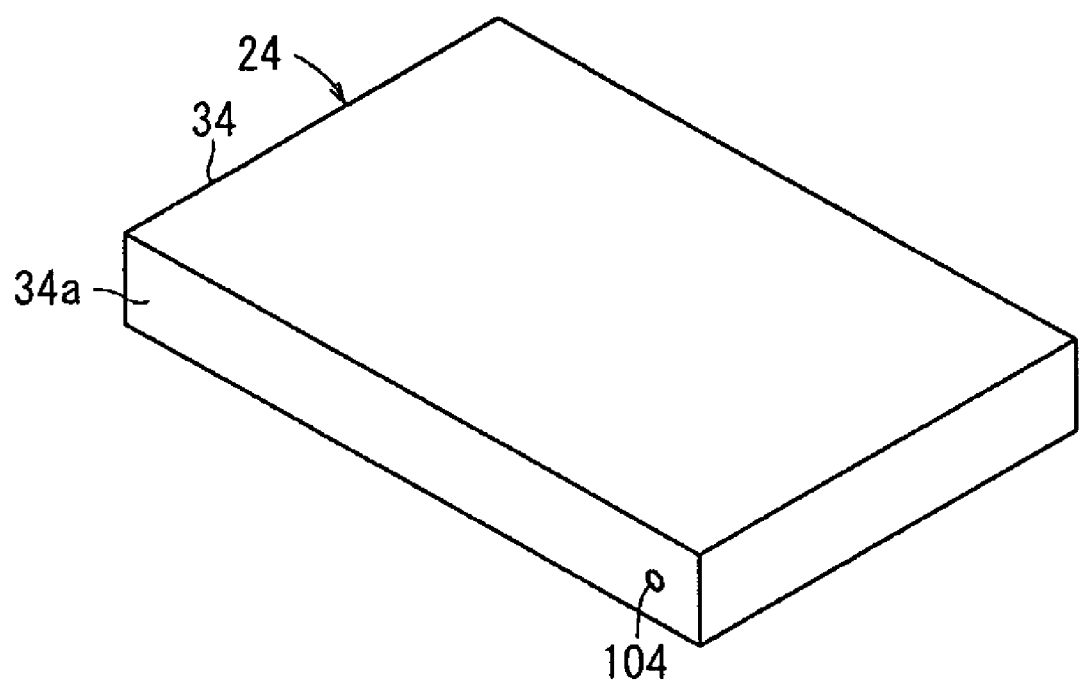
FIG. 5 is a perspective view of the radiation detecting cassette with a light-emitting device mounted on a side thereof.

The cassette 24 houses therein the radiation detector 40, the battery 44, the cassette controller 46, the communication unit 48, and an image memory 102. As shown in FIG. 5, a light-emitting device 104 is mounted on a side 34a of the casing 34 of the cassette 24.

Figure 6:
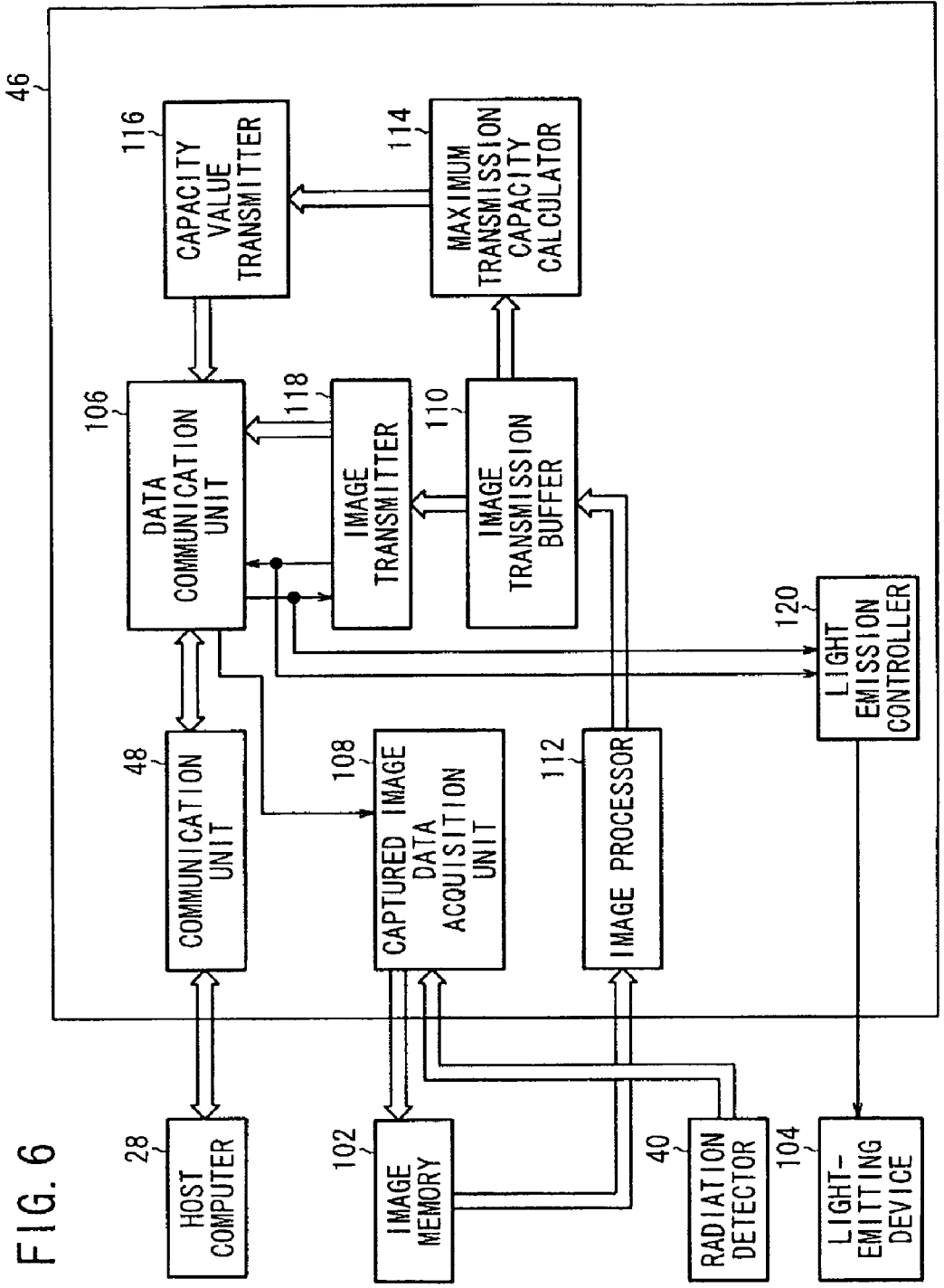
FIG. 6 is a block diagram of a cassette controller of the radiation detecting cassette.

As shown in FIG. 6, the cassette controller 46 comprises a data communication unit 106 for establishing and canceling a link for performing data communications with the host computer 28 and sending and receiving data to and from the host computer 28 through the link, a captured image data acquisition unit 108 for acquiring captured image data (unprocessed raw image data) from the radiation detector 40 by outputting an address signal to the radiation detector 40 based on the reception of an image capturing completion signal from the host computer 28, and storing the acquired image data in the image memory 102, an image transmission buffer 110 for temporarily storing image data to be transmitted, a second image processor 112 for reading out captured image data, of the captured image data stored in the image memory 102, which corresponds to transmission request information from the host computer 28, processing the read captured image data for dark correction, light correction, defect correction, compression, etc., and temporarily storing the processed captured image data in the image transmission buffer 110, a maximum transmission capacity calculator 114 for calculating the amount of image data (capacity value: the number of bits or the number of bytes) stored in the image transmission buffer 110, a capacity value transmitter 116 for transmitting a calculated maximum transmission capacity as text data through the data communication unit 106 to the host computer 28 prior to the transmission of image data, an image transmitter 118 for transmitting the image data stored in the image transmission buffer 110 through the data communication unit 106, and a light emission controller 120 for controlling the light-emitting device 104 to emit light during a period of time in which the image transmitter 118 is transmitting the image data.

Image data to be transmitted refer to the image data stored in the image transmission buffer 110 by the second image processor 112 and also error-correcting code data and quantization table data.

The transmission request information from the host computer 28 represents, for example, image capturing conditions transmitted to the cassette 24 which are required to start capturing a radiation image of the patient, an image capturing completion signal output when the capturing of the radiation image is completed, or an image number that is required irrespectively of the capturing of a radiation image.

If the transmission request information from the host computer 28 represents image capturing conditions, when the next image capturing completion signal is input, the second image processor 112 reads out the latest captured image data stored in the image memory 102, processes the read captured image date as required, and stores the processed captured image data as image data in the image transmission buffer 110.

If the transmission request information from the host computer 28 represents an image number, the second image processor 112 reads out captured image data corresponding to the image number, of the captured image data stored in the image memory 102, processes the read captured image data as required, and stores the processed captured image data as image data in the image transmission buffer 110. The associated relationship between image numbers and image data may be registered in an association table stored in a data memory which is different from the image memory 102. The association table may be edited and updated by the cassette controller 46 when the image data from the radiation detector 40 is recorded in the image memory 102.

When the image data are transmitted to the host computer 28, the cassette ID information and the image number are also transmitted to the host computer 28 to allow the host computer 28 to readily recognize the associated relationship between the image data and the image number. A transmission request for requesting image data to be transmitted based on an image number may be a retransmission request for requesting the image data to be retransmitted or a transmission request for requesting image data of a different data format to be transmitted. If image data that have already been transmitted are uncompressed data, then a transmission request for requesting image data of a different data format is a transmission request for requesting compressed image data to be transmitted. If image data that have already been transmitted are compressed data, then a transmission request for requesting image data of a different data format is a transmission request for requesting uncompressed image data to be transmitted.

When a communication request signal is input from any of various components of the cassette controller 46 to the data communication unit 106, the data communication unit 106 establishes a link with the host computer 28 prior to data communications with the host computer 28. When the data communications with the host computer 28 are over, the data communication unit 106 cancels the link with the host computer 28. After the link with the host computer 28 is canceled, the data communication unit 106 sends a communication completion signal to the source of the communication request signal to notify the source of the completion of the data communications. Specifically, for establishing a link with the host computer 28, the data communication unit 106 outputs an establishment request signal for establishing a link to the host computer 28, and waits for an answer signal from the host computer 28. When the data communication unit 106 receives the answer signal, the link to the host computer 28 is established. Thereafter, actual data are transmitted to and received from the host computer 28. When the transmission and reception of the data are completed, the data communication unit 106 cancels the link. The data communication unit 106 outputs a cancellation request signal for canceling the link to the host computer 28, and waits for an answer signal from the host computer 28. When the data communication unit 106 receives the answer signal, the link to the host computer 28 is canceled.

When the second image processor 112 let the image transmission buffer 110 store processed image data therein, the maximum transmission capacity calculator 114 calculates the number of bits or the number of bytes from the start address of the presently stored image data to EOD (End Of Data) thereof, of the image data stored in the image transmission buffer 110, as a maximum transmission capacity value. The EOD represents a code that is added to the final address of the image data by the second image processor 112. The calculated maximum transmission capacity value is stored in the register of a CPU, for example.

When the calculation of the maximum transmission capacity value by the maximum transmission capacity calculator 114 is finished, the capacity value transmitter 116 reads out the maximum transmission capacity value from the register, and transmits the maximum transmission capacity value through the data communication unit 106 to the host computer 28.

The image transmitter 118 transmits the image data stored in the image transmission buffer 110 through the data communication unit 106 to the host computer 28. Preferably, the image transmitter 118 transmits the image data according to the packet transmission scheme, for example. Specifically, the image transmitter 118 may transmit the image data by dividing the image data into constant lengths of data (constant amounts of data), storing the constant lengths of data in respective packets, and transmitting the packets (first packet transmission process), or may transmit the image data by dividing the image data into variable lengths of data (variable amounts of data), storing the variable lengths of data in respective packets, and transmitting the packets (second packet transmission process). According to the second packet transmission process, the header of each packet may contain information representing the amount of image data stored in the packet, and an EOD code may be added to the final segment of image data stored in each packet.

The light emission controller 120 controls the light-emitting device 104 to emit light during a period of time in which the image transmitter 118 is transmitting image data. Specifically, prior to the transmission of image data from the image transmitter 118, the light emission controller 120 controls the light-emitting device 104 to emit light based on a communication request signal supplied from the image transmitter 118 to the data communication unit 106. After the transmission of the image data is completed, the light emission controller 120 controls the light-emitting device 104 to turn off light based on a communication completion signal supplied from the data communication unit 106 to the image transmitter 118.

Figure 7:
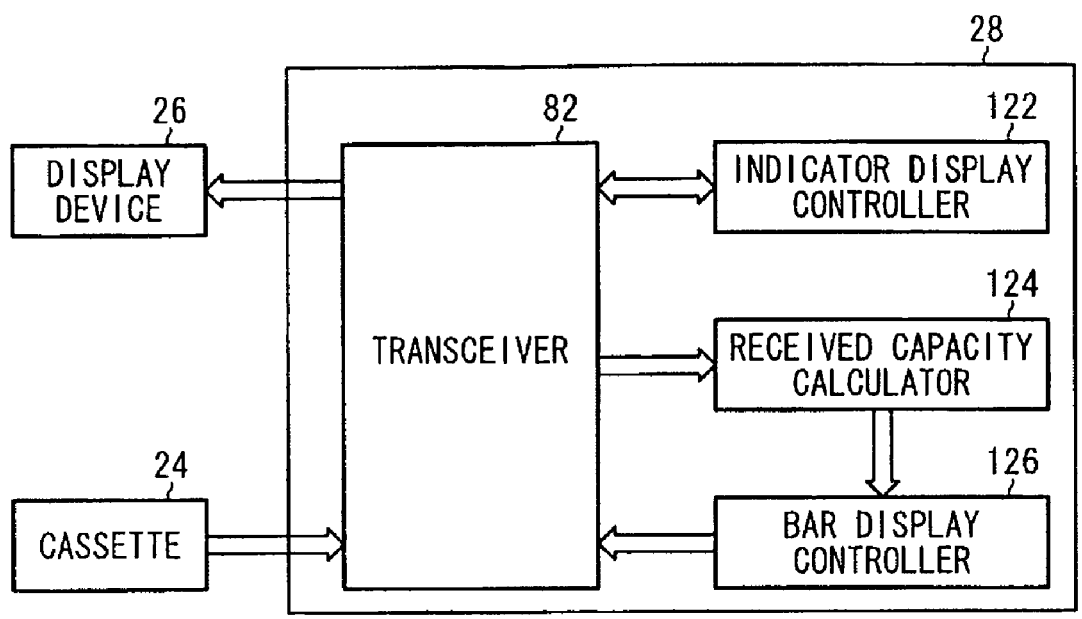
FIG. 7 is a block diagram showing the functions of a host computer for displaying a bar.

As shown in FIG. 7, the host computer 28 includes, in addition to the components described above with reference to FIG. 4, a first indicator display controller 122 for displaying an indicator, which represents the maximum transmission capacity value received from the cassette 24 through the second transceiver 82 as the upper limit, on the display unit 98 of the display device 26, a received capacity calculator 124 for calculating an amount of data (received capacity value) of image data received by the second transceiver 82 during a period of time in which the image data are being received, and a first bar display controller 126 for controlling the display device 26 to display a bar image, which moves toward the displayed indicator and has a length corresponding to the received capacity value of the image data, on the display unit 98.

When the image capturing apparatus 22 finishes capturing an image, the host computer 28 outputs an image capturing completion signal to the cassette 24. The host computer 28 also transmits image capturing conditions to the cassette 24 and the image capturing apparatus 22. Furthermore, the host computer 28 transmits an image number input from the console 27 to the cassette 24. The image capturing conditions and the image number transmitted from the host computer 28 are input as transmission request signal to the cassette 24.

Figure 8:
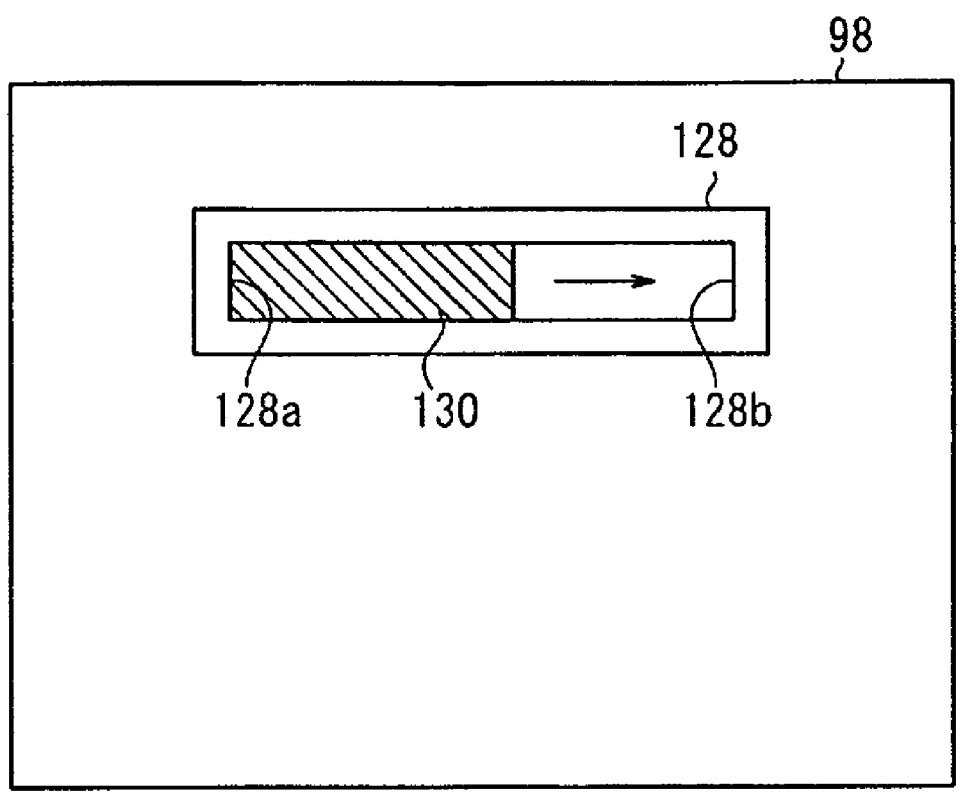
FIG. 8 is a view showing by way of example a frame image and a bar image that are displayed on the display panel of a display device.

The indicator displayed on the display unit 98 of the display device 26 by the first indicator display controller 122 comprises a frame image 128 as shown in FIG. 8, for example. Specifically, the first indicator display controller 122 outputs the frame image 128 that has been generated in advance, together with coordinate data representing a display location, to the display device 26. The display device 26 displays the frame image 128 in the location indicated by the coordinate data on the display unit 98. The first bar display controller 126 displays a bar image 130 that has its start positioned at a left end 128a of the frame image 128 and its end positioned at a right end 128b of the frame image 128.

The received capacity calculator 124 calculates an amount of data of image data received by the second transceiver 82. According to the packet transmission scheme, if the amount of image data contained in the received packets is constant, then the received capacity calculator 124 can obtain the received capacity value up to present by calculating the number of received packets×the constant amount of image data (the number of bits or the number of bytes). If the amount of image data contained in the received packets is variable, then the received capacity calculator 124 can obtain the amount of image data contained in a packet by calculating the amount of image data from the start address of the image data to the EOD code of the packet, and then can obtain the received capacity value up to present by calculating the amount of image data each time a packet is received and accumulating the calculated amounts of image data. If the header of each packet contains information representing the amount of image data stored in the packet, then the received capacity calculator 124 can obtain the received capacity value up to present by accumulating the information representing the amount of image data contained in packet headers each time a packet is received. The received capacity value up to present is stored in the register of the CPU of the host computer 28.

The first bar display controller 126 determines the ratio of the received capacity value up to present to the maximum transmission capacity value from the cassette 24, generates the bar image 130 depending on the determined ratio in the frame image 128, and outputs the bar image 130 together with coordinate data to the display device 26. The display unit 98 of the display device 26 now displays the bar image 130 whose length corresponds to the received capacity value up to present, within the frame image 128. As time passes, since the received capacity value of the image data from the cassette 24 increases, the bar image 130 progressively moves (toward the end 128b of the frame image 128.

Operation of the image capturing system 10 according to the present embodiment will be described below.

The image capturing system 10 is installed in the operating room 12 and used when a radiation image of the patient 14 is required by the surgeons 18 who are performing an operation on the patient 14. Before a radiation image of the patient 14 is captured, patent information of the patient 14 to be imaged is registered in the patient information manager 90 of the host computer 28. If an area of the patient 14 to be imaged and an image capturing method have already been known, such information is registered as image capturing conditions in the image capturing condition manager 84. After the above preparatory process is completed, the surgeons 18 perform an operation on the patient 14.

For capturing a radiation image of the patient 14 during the operation, one of the surgeons 18 or the radiological technician places the radiation detecting cassette 24 in a given position between the patient 14 and the surgical table 16 with the irradiated surface 36 facing the image capturing apparatus 22. Then, after having moved the image capturing apparatus 22 to a position confronting the cassette 24, one of the surgeons 18 or the radiological technician turns on the image capturing switch 74 to capture a radiation image of the patient 14.

The radiation source controller 80 of the image capturing apparatus 22 controls the radiation source 76 according to the image capturing condition about the area of the patient to be imaged which is received through the first transceiver 78, to apply a radiation X at a given dosage to the patient 14.

The radiation X which has passed through the patient 14 is applied to the grid 38, which removes scattered rays from the radiation X. Then, the radiation X is applied to the radiation detector 40, and converted into electric signals by the photoelectric conversion layer 51 of the pixels 50 of the radiation detector 40. The electric signals are stored as electric charges in the storage capacitors 53 (see FIG. 3). The stored electric charges, which represent radiation image information of the patient 14, are read out from the storage capacitors 53 according to address signals which are supplied from the captured image data acquisition unit 108 of the cassette controller 46 to the line scanning driver 58 and the multiplexer 66.

Specifically, in response to the address signal supplied from the captured image data acquisition unit 108, the row address decoder 60 of the line scanning driver 58 outputs a selection signal to select one of the first switches SW1, which supplies the control signal Von to the gates of the TFTs 52 connected to the gate line 54 corresponding to the selected first switch SW1. On the other hand, in response to the address signal supplied from the captured image data acquisition unit 108, the column address decoder 68 of the multiplexer 66 outputs a selection signal to successively turn on the second switches SW2 to switch between the signal lines 56 for thereby reading out the electric charges stored in the storage capacitors 53 of the pixels 50 connected to the selected gate line 54, through the signal lines 56.

The electric charges representing the radiation image information (captured image data) read out from the storage capacitors 53 of the pixels 50 connected to the selected gate line 54 of the radiation detector 40 are amplified by the respective amplifiers 62, sampled by the sample and hold circuits 64, and supplied to the multiplexer 66. Based on the supplied electric charges, the multiplexer 66 generates and supplies a radiation image signal to the A/D converter 70, which converts the radiation image signal into a digital signal. The digital signal which represents the radiation image information is stored in the image memory 102 of the cassette controller 46.

Similarly, the row address decoder 60 of the line scanning driver 58 successively turns on the first switches SW1 to switch between the gate lines 54 according to the address signal supplied from the captured image data acquisition unit 108. The electric charges stored in the storage capacitors 53 of the pixels 50 connected to the successively selected gate lines 54 are read out through the signal lines 56, and processed by the multiplexer 66 and the A/D converter 70 into digital signals. The digital signals which represent the radiation image information (captured image data) are stored in the image memory 102 of the cassette controller 46.

Based on the reception of an image capturing completion signal output from the host computer 28, the second image processor 112 reads out the latest captured image data stored in the image memory 102, processes the latest captured image data into image data, and stores the processed image data in the image transmission buffer 110.

When the second image processor 112 stores the image data in the image transmission buffer 110, the maximum transmission capacity calculator 114 calculates a capacity value of the image data (maximum transmission capacity value) and stores the calculated maximum transmission capacity value in the register.

When the maximum transmission capacity calculator 114 finishes the calculation of the maximum transmission capacity value, the capacity value transmitter 116 reads out the maximum transmission capacity value from the register and transmits the read maximum transmission capacity value through the data communication unit 106 to the host computer 28.

Thereafter, the image transmitter 118 transmits the image data stored in the image transmission buffer 110 through the data communication unit 106 to the host computer 28.

During the transmission of the image data, the light-emitting device 104 mounted on the side 34a of the casing 34 emits light under the control of the light emission controller 120. Therefore, the surgeons 18 and the radiological technician are able to recognize that the image data are being transmitted to the host computer by seeing that the light-emitting device 104 on the cassette 24 is emitting light.

Based on the maximum transmission capacity value transmitted prior to the image data, the first indicator display controller 122 of the host computer 28 controls the display device 26 to display the frame image 128.

While the image data are subsequently being received, the received capacity calculator 124 calculates a received capacity value of the image data, and the first bar display controller 126 controls the display device 26 to display the bar image 130 whose length depends on the ratio of the received capacity value to the maximum transmission capacity value.

Consequently, the surgeons 18 and the radiological technician are able to recognize at once the communication status of the image data by seeing the bar image 130 displayed on the display unit 98 of the display device 26. The display of the bar image 130 is particularly effective to recognize the communication status of the image data if the light emission from the light-emitting device 104 is difficult to recognize for some reasons, and the length of the bar image 130 gives a clear intuitive indication of how the transmission of the image data is in progress.

Since the maximum transmission capacity value of the image data is transmitted as text data prior to the transmission of the image data, the ratio of the already received capacity value to the maximum transmission capacity value can accurately be determined for the generation of the bar image 130 in the first bar display controller 126, so that the progress of the transmission of the image data which will subsequently be sent can accurately be displayed as a bar image. As a result, it is possible to avoid the bar image 130 from stopping moving somewhere short of the terminal end, though the transmission of the image data is completed, and the surgeons 18 and the radiological technician can accurately recognize how the transmission of the image data is in progress.

When the reception of the image data is completed, the image data are processed by the first image processor 86 and then stored, in association with the patient information of the patient 14 registered in the patient information manager 90, in the image memory 88.

The processed image data are transmitted from the second transceiver 82 to the display device 26. When the display device 26 has received the image data through the receiver 94, the display controller 96 controls the display unit 98 to display a radiation image based on the image data. The surgeons 18 perform a surgical operation on the patient 14 while watching the radiation image displayed on the display unit 98.

Since no cables for transmitting and receiving signals are connected between the cassette 24 and the host computer 28, between the image, capturing apparatus 22 and the host computer 28, and between the host computer 28 and the display device 26, it is not necessary to lay such cables on the floor of the operating room 12 and hence there are no cable-induced obstacles to the operation performed by the surgeons 18, the radiological technician, or other staff members in the operating room 12.

In the image capturing system 10 according to the present embodiment, as described above, since the transmission of the image data from the cassette 24 to the host computer 28, whether it is in progress or it is completed, can easily be recognized based on the light emission of the light-emitting device 104 on the cassette 24 and the bar image 130 displayed on the display unit 98 of the display device 26. Accordingly, it is unlikely for the user to accidentally remove the battery pack 45 from the cassette 24 or for the operator of the host computer 28 to initiate a next process while the image data are being transmitted.

Figure 9:
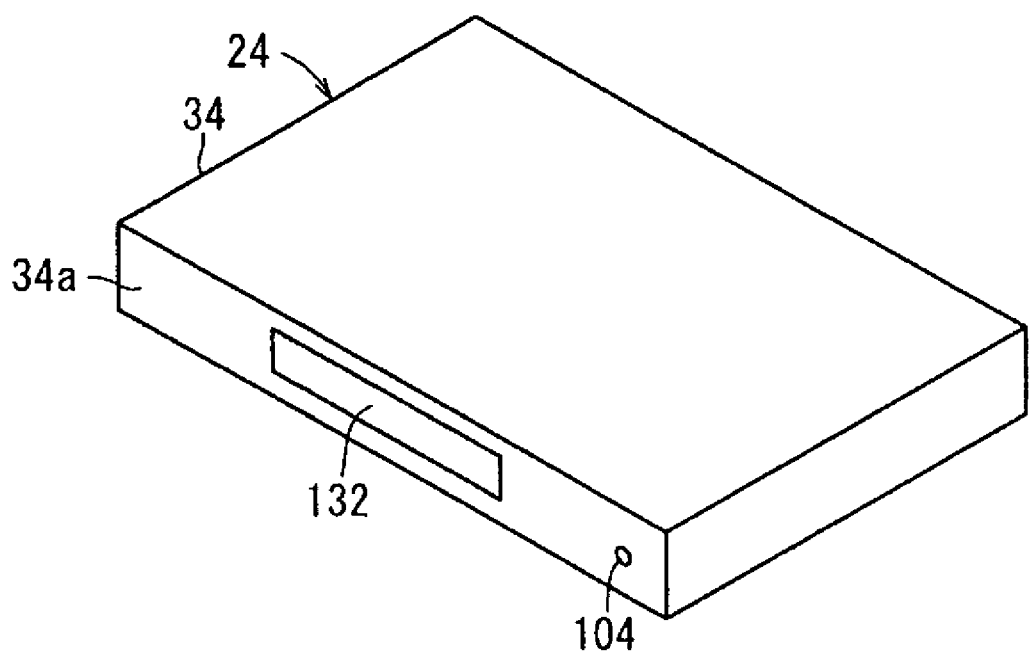
FIG. 9 is a perspective view of a radiation detecting cassette with a liquid crystal display mounted on a side thereof.
Figure 10:
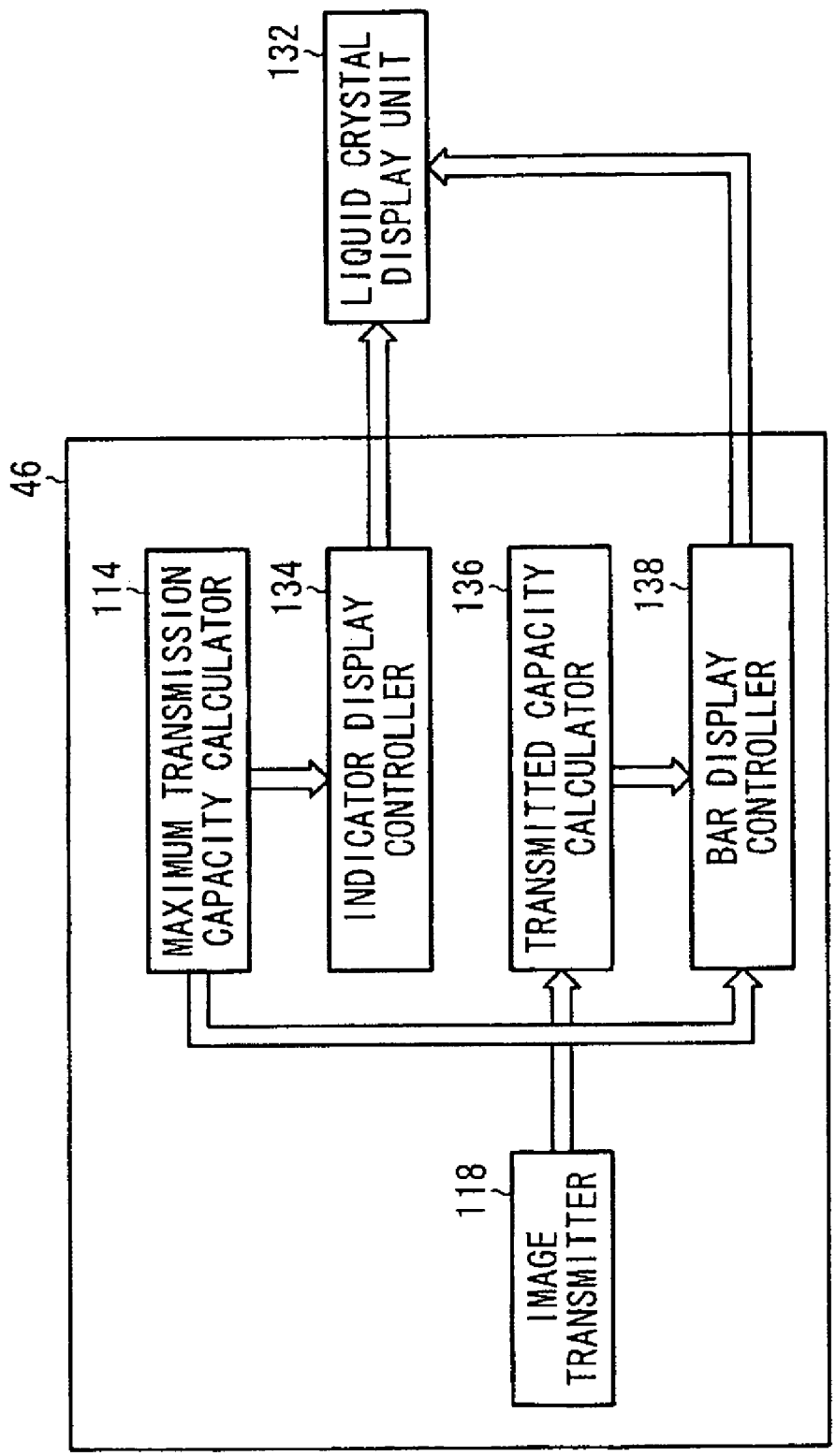
FIG. 10 is a block diagram of a cassette controller, partly omitted from illustration, for controlling the liquid crystal display shown in FIG. 9.

In the above embodiment, the light-emitting device 104 is mounted on the cassette 24. As shown in FIG. 9, in addition to the light-emitting device 104, a liquid crystal display unit 132 may also be mounted on the side 34a of the casing 34 of the cassette 24. In this case, as shown in FIG. 10, the cassette controller 46 additionally includes a second indicator display controller 134 for displaying an indicator, which represents the maximum transmission capacity value calculated by the maximum transmission capacity calculator 114 as the upper limit, on the liquid crystal display unit 132, a transmitted capacity calculator 136 for calculating an amount of data (transmitted capacity value) of image data transmitted by the image transmitter 118 during a period of time in which the image data are being transmitted, and a second bar display controller 138 for controlling the liquid crystal display unit 132 to display a bar image, which has a length corresponding to the transmitted capacity value of the image data. In FIG. 10, the image transmission buffer 110 and some other components shown in FIG. 6 are omitted from illustration.

Figure 11:
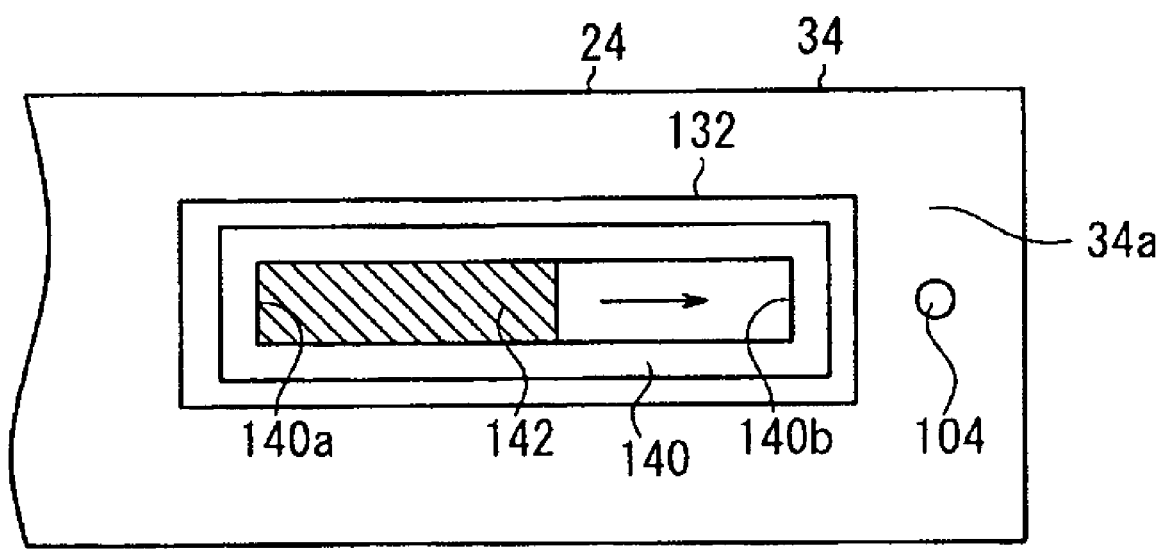
FIG. 11 is a view showing by way of example a frame image and a bar image that are displayed on the liquid crystal display.

The indicator displayed on the liquid crystal display unit 132 by the second indicator display controller 134 comprises a frame image 140 as shown in FIG. 11, for example. Specifically, the second indicator display controller 134 outputs the frame image 140 that has been generated in advance, together with coordinate data representing a display location, to the liquid crystal display unit 132. The liquid crystal display unit 132 displays thereon the frame image 140 in the location indicated by the coordinate data. The second bar display controller 138 displays a bar image 142 that has its start positioned at a left end 140a of the frame image 140 and its end positioned at a right end 140b of the frame image 140.

The transmitted capacity calculator 136 calculates an amount of data of image data transmitted by the image transmitter 118. According to the packet transmission scheme, if the amount of image data contained in the transmitted packets is constant, then the transmitted capacity calculator 136 can obtain the transmitted capacity value up to present by calculating the number of transmitted packets×the constant amount of image data (the number of bits or the number of bytes). If the amount of image data contained in the transmitted packets is variable, then the transmitted capacity calculator 136 can obtain the amount of image data contained in a packet by calculating the amount of image data from the start address of the image data to the EOD code of the packet, and then can obtain the transmitted capacity value up to present by calculating the amount of image data each time a packet is transmitted and accumulating the calculated amounts of image data. If the header of each packet contains information representing the amount of image data stored in the packet, then the transmitted capacity calculator 136 can obtain the transmitted capacity value up to present by accumulating the information representing the amount of image data contained in packet headers each time a packet is received. The transmitted capacity value up to present is stored in the register of the CPU of the cassette controller 46, for example.

The second bar display controller 138 determines the ratio of the transmitted capacity value up to present to the maximum transmission capacity value from the cassette 24, generates the bar image 142 depending on the determined ratio in the frame image 140, and outputs the bar image 142 together with coordinate data to the liquid crystal display unit 132. The liquid crystal display unit 132 now displays the bar image 142 whose length corresponds to the transmitted capacity value up to present, within the frame image 140. As time passes, since the transmitted capacity value of the image data from the cassette 24 increases, the bar image 142 progressively moves toward the end 140b of the frame image 140.

When the operator who handles the cassette 24 returns the cassette 24 after having captured a radiation image therein, the operator can recognize that the image data are being transmitted from the cassette 24 by seeing the light emission of the light-emitting device 104, preventing the operator from accidentally removing the battery pack 45 from the cassette 24. The operator can also clearly recognize how the transmission of the image data is in progress by seeing the bar image 142, which is commensurate with the transmitted capacity value, displayed on the liquid crystal display unit 132 on the cassette 24.

Preferred structural details of the image capturing system 10 according to the present embodiment, particularly the cassette 24, will be described below.

The casing 34 of the cassette 24 should preferably have a communication sustaining means for sustaining the transmission of image data during a period of time in which the image data are being transmitted.

Figure 12:
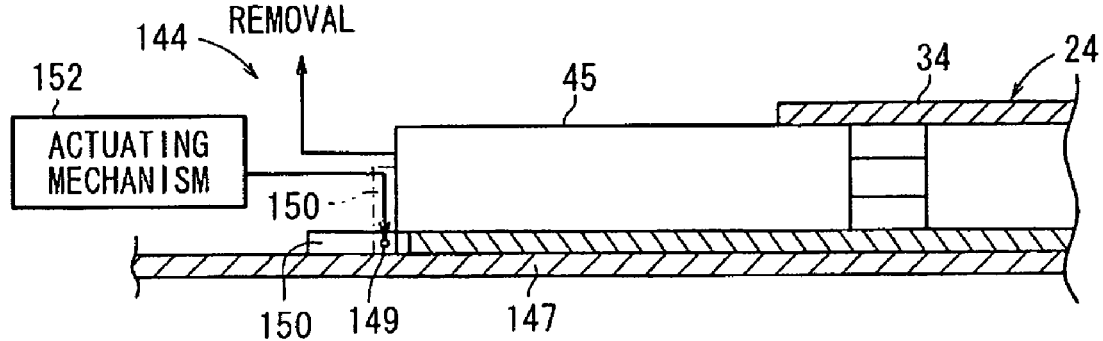
FIG. 12 is a diagram of a first lock mechanism.

As shown in FIG. 12, when the battery pack 45 is attached to the casing 34, the communication sustaining means includes a first lock mechanism 144 for locking the battery pack 45 against removal from the casing 34 at least during a period of time in which the image data are being transmitted.

The first lock mechanism 144 comprises a stopper plate 150 having a rectangular, semicircular, or polygonal shape, for example, mounted on a bottom plate 147 of the casing 34 and angularly movable about a shaft 149, and a first actuating mechanism 152 (solenoid or electric motor) for angularly moving the stopper plate 150 selectively in two directions, i.e., a first direction for pressing the battery pack 45 and a second direction for releasing the battery pack 45. The first direction should preferably be a direction to prevent the battery pack 45 from moving. For example, if the battery pack 45 is removed from the casing 34 when it is moved horizontally, as shown in FIG. 12, then the stopper plate 150 should preferably press a part of the battery pack 45 so as to prevent it from moving horizontally. The second direction should preferably be a direction to release the battery pack 45 from a pressed state to allow it to move horizontally smoothly.

If the first actuating mechanism 152 comprises a solenoid, not shown, then the stopper plate 150 is normally urged to move in the second direction to release the battery pack 45 by a leaf spring, not shown, connected to the stopper plate 150 while the solenoid is de-energized. At least while the image data are being transmitted, the solenoid is energized to turn the stopper plate 150 in the first direction against the bias of the leaf spring, thereby pressing the battery pack 45 against removal from the casing 34. If the first actuating mechanism 152 comprises an electric motor, not shown, coupled to the shaft 149 for turning the stopper plate 150 selectively in the first and second directions, then the stopper plate 150 is turned in the second direction when the electric motor is energized to rotate the shaft 149 in one direction, and the stopper plate 150 is turned in the first direction when the electric motor is energized to reverse the shaft 149 in the other direction.

Figure 13:
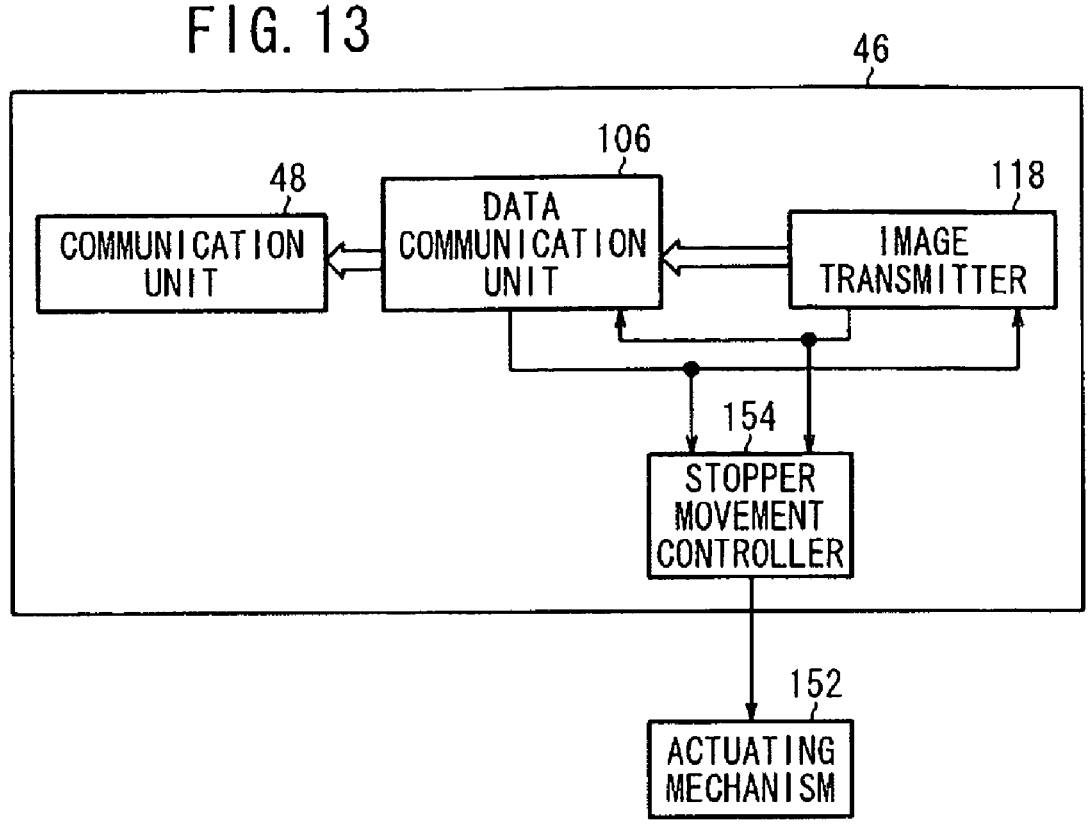
FIG. 13 is a block diagram of a cassette controller, partly omitted from illustration, for controlling the first lock mechanism shown in FIG. 12.

As shown in FIG. 13, the cassette controller 46 has a stopper movement controller 154. In FIG. 13, the image transmission buffer 110 and some other components shown in FIG. 6 are omitted from illustration.

Prior to the transmission of image data from the image transmitter 118, the stopper movement controller 154 controls the first actuating mechanism 152 to turn the stopper plate 150 in the first direction to press the battery pack 45 based on a communication request signal output from the image transmitter 118 to the data communication unit 106. After the transmission of image data is completed, the stopper movement controller 154 controls the first actuating mechanism 152 to turn the stopper plate 150 in the second direction to release the battery pack 45 based on a communication completion signal output from the data communication unit 106 to the image transmitter 118.

Therefore, at least while the image data are being transmitted, the battery pack 45 cannot be removed from the casing 34. The battery pack 45 is thus prevented from being accidentally pulled out of the casing 34 during the transmission of the image data.

The communication sustaining means may be of another structure applicable to a cable connected to the cassette 24. With the previous structure shown in FIG. 12, the various components housed in the cassette 24 are supplied with electric power from the battery 44 housed in the battery pack 45 placed in the cassette 24. However, the various components housed in the cassette 24 may be supplied with electric power from an external power supply through a power cable. Alternatively, the various components housed in the cassette 24 may be supplied with electric power from the battery 44, and the cassette 24 may communicate with the host computer 28 through a communication cable.

If such a power cable or a communication cable is connected to the cassette 24, then the cable should not be detached while the image data are being transmitted.

Figure 14:
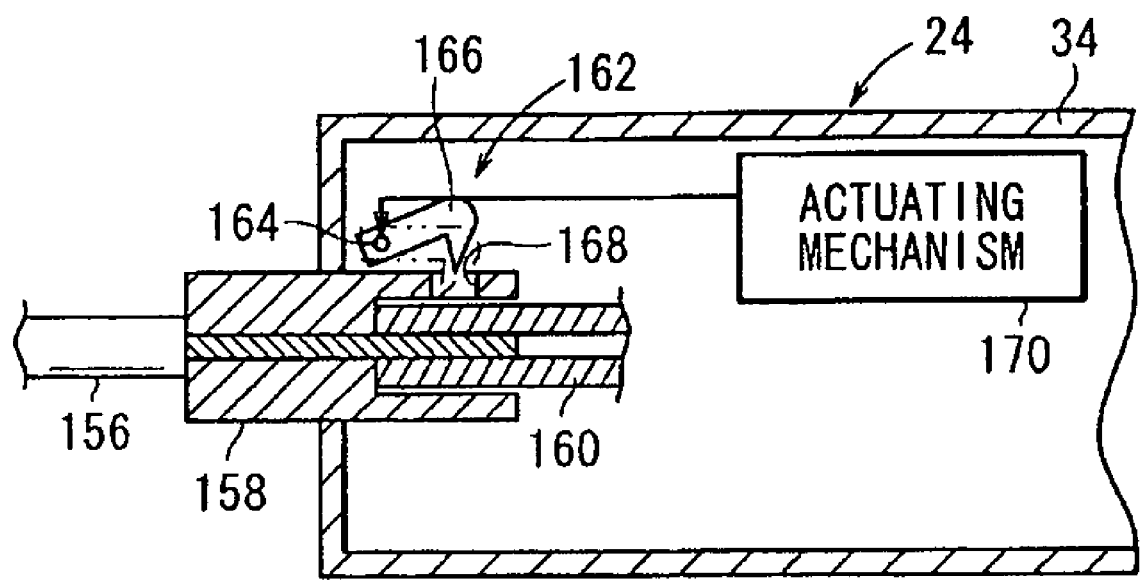
FIG. 14 is a diagram of a second lock mechanism.

As shown in FIG. 14, a cable 156 has a plug 158 inserted in the casing 34 and fitted over a connector 160 of the cassette 24. The communication sustaining means of the other structure comprises a second lock mechanism 162 for preventing the cable 156 from being disconnected from the cassette 24 at least while the image data are being transmitted.

The second lock mechanism 162 comprises a wedge-shaped hook 166 disposed near the connector 160 and angularly movable about a shaft 164, and a second actuating mechanism 170 (solenoid or electric motor) for angularly moving the hook 166 selectively in two directions, i.e., a first direction to engage in a hole 168 defined in the plug 158 and a second direction to disengage from the hole 168 defined in the plug 158. When the hook 166 engages in the hole 168, the cable 156 cannot easily be detached from the cassette 24.

If the second actuating mechanism 170 comprises a solenoid, not shown, then the hook 166 is normally urged to turn in the second direction to move out of the hole 168 by a leaf spring, not shown, connected to the hook 166 while the solenoid is de-energized. At least while the image data are being transmitted, the solenoid is energized to turn the hook 166 in the first direction against the bias of the leaf spring, thereby placing the hook 166 in the hole 168. If the second actuating mechanism 170 comprises an electric motor, not shown, coupled to the shaft 164 for turning the hook 166 selectively in the first and second directions, then the hook 166 is turned in the second direction when the electric motor is energized to rotate the shaft 164 in one direction, and the hook 166 is turned in the first direction when the electric motor is energized to reverse the shaft 164 in the other direction.

Figure 15:
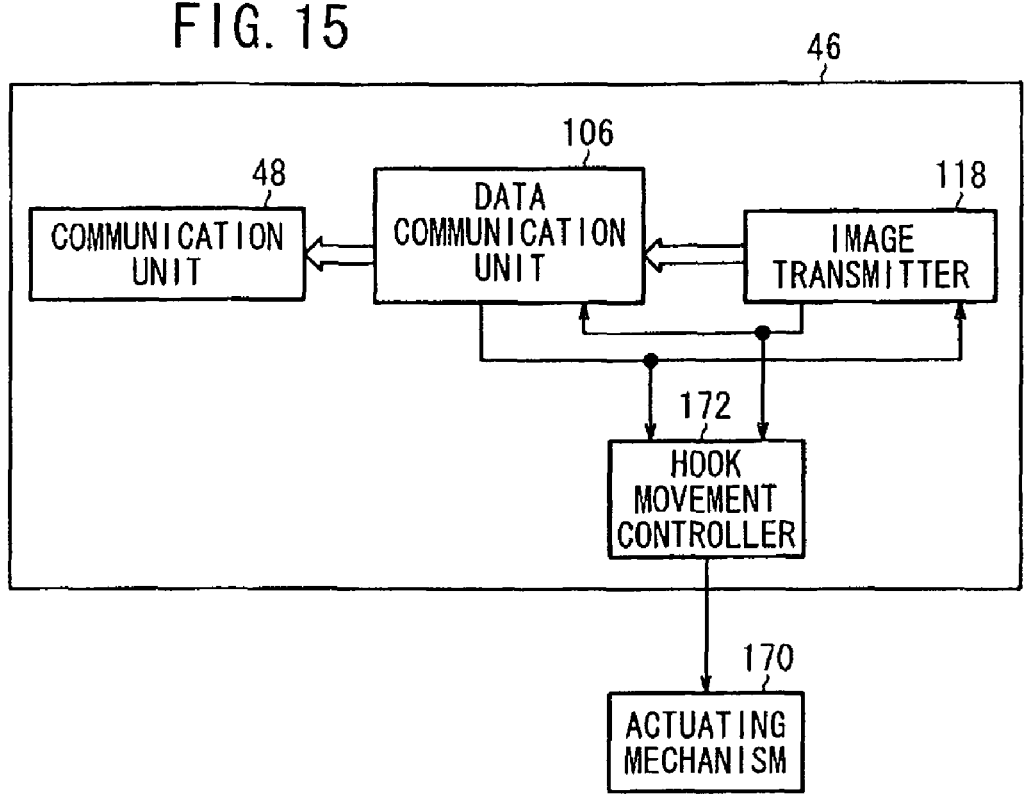
FIG. 15 is a block diagram of a cassette controller, partly omitted from illustration, for controlling the second lock mechanism shown in FIG. 14.

As shown in FIG. 15, the cassette controller 46 has a hook movement controller 172. In FIG. 15, the image transmission buffer 110 and some other components shown in FIG. 6 are omitted from illustration.

Prior to the transmission of image data from the image transmitter 118, the hook movement controller 172 controls the second actuating mechanism 170 to turn the hook 166 in the first direction to place the hook 166 in the hole 168 based on a communication request signal output from the image transmitter 118 to the data communication unit 106. After the transmission of image data is completed, the hook movement controller 172 controls the second actuating mechanism 170 to turn the hook 166 in the second direction to move out of the hole 168 based on a communication completion signal output from the data communication unit 106 to the image transmitter 118.

Therefore, at least while the image data are being transmitted, the cable 156 cannot be detached from the casing 34. The cable 156 is thus prevented from being accidentally disconnected from the cassette 24 during the transmission of the image data.

In the radiation image capturing system 10 according to the illustrated embodiment, the radiation detector 40 housed in the cassette 24 directly converts the dosage of the applied radiation X into an electric signal with the photoelectric conversion layer 51. However, the radiation image capturing system 10 may employ a radiation detector including a scintillator for converting the applied radiation X into visible light and a solid-state detecting device such as of amorphous silicon (a-Si) or the like for converting the visible light into an electric signal (see Japanese patent No. 3494683).

Alternatively, the radiation image capturing system 10 may employ a light-conversion radiation detector for acquiring radiation image information. The light-conversion radiation detector operates as follows: When a radiation is applied to a matrix of solid-state detecting devices, and the solid-state detecting devices store an electrostatic latent image depending on the dosage of the applied radiation. For reading the stored electrostatic latent image, reading light is applied to the solid-state detecting devices to cause the solid-state detecting devices to generate electric current representing radiation image information. When erasing light is applied to the radiation detector, radiation image information representing a residual electrostatic latent image is erased from the radiation detector, which can thus be reused (see Japanese Laid-Open Patent Publication No. 2000-105297).

When the cassette 24 is used in the operating room 12 or the like, the cassette 24 may be subjected to adhesion of blood, contamination, etc. However, when the radiation detecting cassette 24 is designed to have a waterproof and hermetically-sealed structure, and is sterilized and cleaned as necessary, one cassette 24 can be used repeatedly.

The cassette 24 is not limited to use in the operating room 12, and may be used for a medical examination and a round in the hospital.

Also, the cassette 24 may communicate with external devices via optical wireless communication using infrared light or the like, instead of general wireless communication using radio wave.

Figure 16:
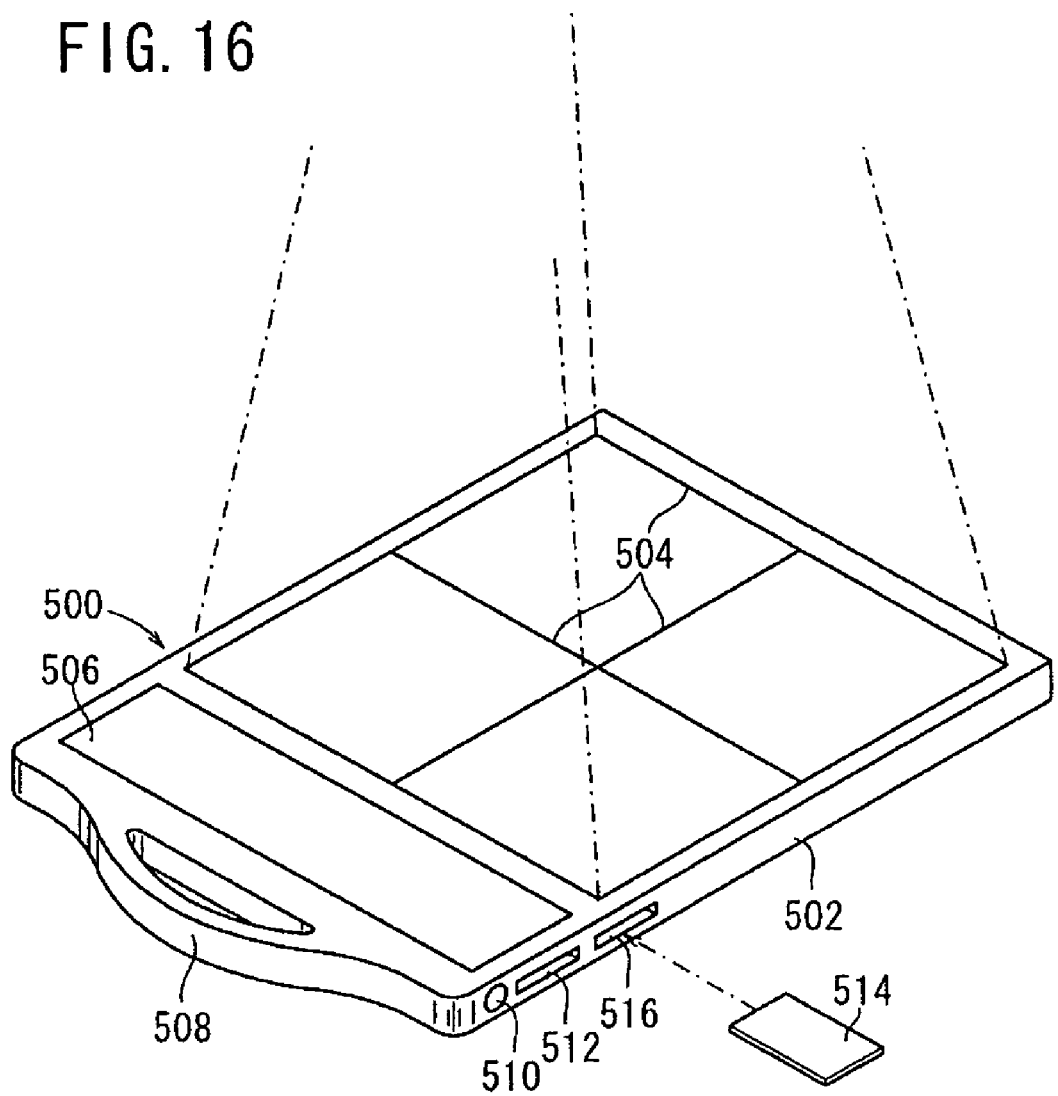
FIG. 16 is a perspective view showing a radiation detecting cassette according to another embodiment of the present invention.

Preferably, the cassette 500 may be constructed as shown in FIG. 16.

Specifically, the cassette 500 includes a guiding line 504 drawn on the radiation-irradiated surface of a casing 502, the guiding line 504 serving as a reference for setting a captured area and a captured position. Using the guiding line 504, a subject 14 can be positioned with respect to the cassette 500, and an area irradiated with the radiation X can be set, thereby recording radiation image information on an appropriate captured area.

The cassette 500 is provided with a display section 506 on an area thereof other than the captured area, for displaying various information about the cassette 500. The information which is displayed on the display section 506, includes ID information of a subject 14 whose radiation image information is to be recorded on the cassette 500, the number of times the cassette 500 has been used, an accumulated exposed radiation dose, a charging state (remaining battery level) of a battery 44 in the cassette 500, image capturing conditions of radiation image information, and a positioning image of the subject 14 with respect to the cassette 500. In this case, a technician confirms a subject 14 based on the ID information displayed on the display section 506, for example, and also previously confirms that the cassette 500 is placed in a usable state. Then, the technician positions a desired captured area of the subject 14 with respect to the cassette 500 based on the displayed positioning image, thereby capturing appropriate radiation image information.

Also, the cassette 500 is provided with a handgrip 508, whereby it is easier to handle and carry the cassette 500.

Preferably, the cassette 500 may have, on a side thereof, an input terminal 510 for an AC adapter, a USB (Universal Serial Bus) terminal 512, and a card slot 516 for inserting a memory card 514.

When the charging function of the battery 44 in the cassette 500 becomes deteriorated, or when there is not enough time to fully charge the battery 44, the input terminal 510 is connected to the AC adapter to externally supply the cassette 500 with electric power, thereby enabling the cassette 500 to be used immediately.

The USB terminal 512 or the card slot 516 may be used when the cassette 500 cannot transmit and receive information to and from external devices such as the host computer 28 via wireless communication. Specifically, by connecting a cable to the USB terminal 512, the cassette 500 can transmit and receive information to and from the external devices via wire communication. Alternatively, the memory card 514 is inserted into the card slot 516, and necessary information is recorded on the memory card 514. After that, the memory card 514 is removed from the card slot 516, and the memory card 514 is inserted into the external device, thereby enabling information to be transferred.

Figure 17:
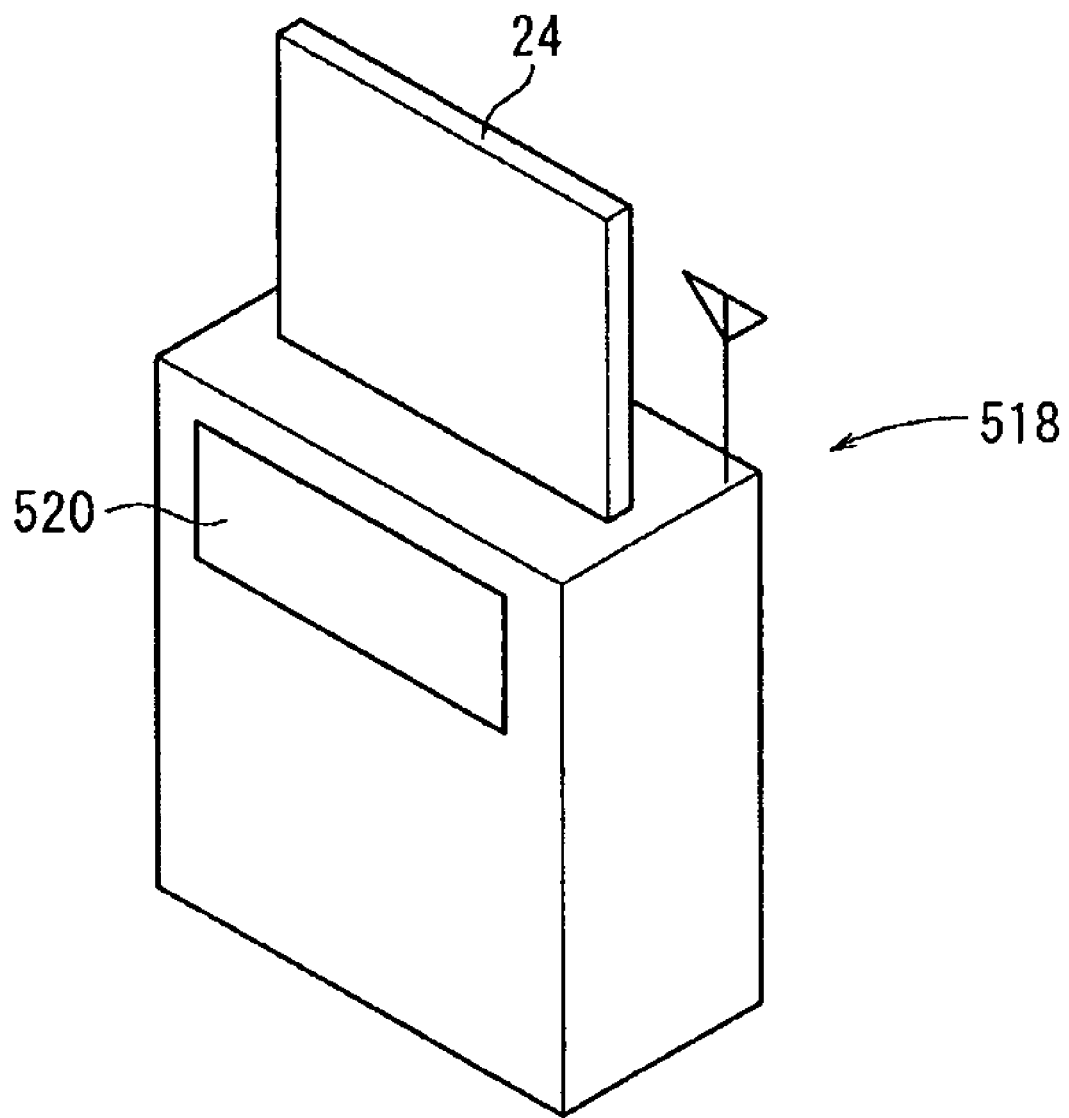
FIG. 17 is a perspective view showing a cradle which charges the radiation detecting cassette.

Preferably, a cradle 518 may be disposed in the operating room 12 or at a desired place in the hospital, into which the cassette 24 is inserted to charge the internal battery 44, as shown in FIG. 17. In this case, in addition to charging the battery 44, the cradle 518 may transmit and receive necessary information to and from external devices such as HIS 148, RIS 146, the host computer 28, etc. by way of wireless or wire communications of the cradle 518. The information may include radiation image information which is recorded on the cassette 24 inserted into the cradle 518.

Also, the cradle 518 may be provided with a display section 520. The display section 520 may display necessary information including a charging state of the inserted cassette 24 and radiation image information acquired from the cassette 24.

Further, a plurality of cradles 518 may be connected to a network. In this case, information about charging states of cassettes 24 inserted in respective cradles 518 can be collected through the network, and the cassette 24 in a usable state can be located.

Although certain preferred embodiments of the present invention have been shown and described in detail, it should be understood that various changes and modifications may be made therein without departing from the scope of the appended claims.

The invention claimed is:

1. A medical system comprising:
   a radiation detecting cassette having:
     a casing;
     a radiation conversion panel housed in said casing for detecting a radiation that has passed through a subject and converting the detected radiation into radiation image information;
     a memory housed in said casing for storing the radiation image information converted by said radiation conversion panel;
     a communication unit housed in said casing for transmitting at least said radiation image information to an external device; and
     a cassette controller housed in said casing, said medical system further comprising:
   a communication sustaining unit housed in said casing of said radiation detecting cassette and adapted to keep said radiation image information transmitted at least during a period of time in which said communication unit is transmitting said radiation image information, and
   a display unit which displays that said radiation image information is being transmitted from said communication unit during said period of time in which said communication unit is transmitting said radiation image information.

2. A medical system according to claim 1, wherein said display unit is mounted on a surface of said casing of said radiation detecting cassette.

3. A medical system according to claim 1, further comprising:
   an image capturing apparatus adapted to radiate the radiation to said subject; and
   a computer adapted to exchange information with said radiation detecting cassette and control said image capturing apparatus,
   wherein said display unit is connected to said computer.

4. A medical system according to claim 1, further comprising a cradle adapted to charge a battery housed in said radiation detecting cassette, wherein
   said display unit is mounted on a surface of said cradle.

5. A medical system according to claim 1, wherein said display unit comprises a light-emitting device adapted to emit light during said period of time in which said communication unit is transmitting said radiation image information.

6. A medical system according to claim 1, wherein said display unit comprises an indicator representing an upper limit of a capacity value of said radiation image information transmitted by said communication unit, and a bar image, which moves toward said indicator so as to have a length corresponding to the received capacity value of said radiation image information during said period of time in which said communication unit is transmitting said radiation image information.

7. A medical system according to claim 1, further comprising a battery pack housed in said casing,
   wherein said communication sustaining unit comprises a lock mechanism for preventing said battery pack from being removed out of said casing at least during said period of time in which said communication unit is transmitting said radiation image information.

8. A medical system according to claim 1, further comprising a connector housed in said casing for connecting to a cable, wherein said communication sustaining unit comprises a lock mechanism for preventing said cable from being disconnected from said connector at least during said period of time in which said communication unit is transmitting said radiation image information.

9. A medical system according to claim 1, wherein said communication sustaining unit comprises a mechanism for preventing detachment of a device necessary for said communication unit to transmit said radiation image information.

10. A medical system according to claim 9, wherein the device is a battery pack housed in said casing.

11. A medical system according to claim 9, wherein the device is a power cable connected to a connector housed in said casing.

12. A medical system according to claim 9, wherein the device is a communication cable connected to a connector housed in said casing.

13. A radiation detecting cassette having:
 a casing;
 a radiation conversion panel housed in said casing for detecting a radiation that has passed through a subject and converting the detected radiation into radiation image information;
 a memory housed in said casing for storing the radiation image information converted by said radiation conversion panel;
 a communication unit housed in said casing for transmitting at least said radiation image information to an external device;
 a cassette controller housed in said casing;
 a communication sustaining unit housed in said casing adapted to keep said radiation image information transmitted at least during a period of time in which said communication unit is transmitting said radiation image information, and
 a display unit mounted on said casing and which displays that said radiation image information is being transmitted from said communication unit during said period of time in which said communication unit is transmitting said radiation image information.

14. A radiation detecting cassette according to claim 13, wherein said display unit comprises a light-emitting device adapted to emit light during said period of time in which said communication unit is transmitting said radiation image information.

15. A radiation detecting cassette according to claim 13, wherein said display unit comprises an indicator representing an upper limit of a capacity value of said radiation image information transmitted by said communication unit, and a bar image, which moves toward said indicator so as to have a length corresponding to the received capacity value of said radiation image information during said period of time in which said communication unit is transmitting said radiation image information.

* * * * *